(12) United States Patent
Schreyer et al.

(10) Patent No.: US 9,927,416 B2
(45) Date of Patent: Mar. 27, 2018

(54) METHOD FOR CONTROLLING A DISINFECTION STATUS OF A TEMPERATURE CONTROL DEVICE AND TEMPERATURE CONTROL DEVICE FOR HUMAN BODY TEMPERATURE CONTROL DURING EXTRACORPOREAL CIRCULATION

(71) Applicant: Sorin Group Deutschland GmbH, München (DE)

(72) Inventors: Johann Schreyer, München (DE); Erwin Knott, Poing (DE)

(73) Assignee: Sorin Group Deutschland GmbH, Munich (DE)

( * ) Notice: Subject to any disclaimer, the term of this patent is extended or adjusted under 35 U.S.C. 154(b) by 0 days.

(21) Appl. No.: 15/008,164

(22) Filed: Jan. 27, 2016

(65) Prior Publication Data

US 2016/0139100 A1    May 19, 2016

Related U.S. Application Data

(63) Continuation of application No. 14/421,438, filed as application No. PCT/EP2013/065601 on Jul. 24, 2013, now Pat. No. 9,259,523.

(30) Foreign Application Priority Data

Aug. 13, 2012 (EP) .................................... 12180231

(51) Int. Cl.
*B08B 9/00* (2006.01)
*A61M 37/00* (2006.01)
(Continued)

(52) U.S. Cl.
CPC ................ *G01N 33/18* (2013.01); *A61L 2/16* (2013.01); *A61L 2/18* (2013.01); *A61L 2/186* (2013.01);
(Continued)

(58) Field of Classification Search
CPC .. A61L 2/00; A61L 2/186; A61L 2/208; C02F 3/00; C02F 1/50
(Continued)

(56) References Cited

U.S. PATENT DOCUMENTS 3,064,649 A    11/1962  Fuson
4,180,896 A     1/1980  Reed et al.
(Continued)

FOREIGN PATENT DOCUMENTS

CN         1202116 A    12/1988
CN       201871012 U     6/2011
(Continued)

OTHER PUBLICATIONS

English translations of the description section and the claims of FR 2631241.*

(Continued)

*Primary Examiner* — Monzer R Chorbaji
(74) *Attorney, Agent, or Firm* — Faegre Baker Daniels LLP

(57) ABSTRACT

The present application relates to a method for controlling a disinfection status of a heater and/or cooler for human body temperature control during extracorporeal circulation. The temperature control is conducted by use of a heat exchanger and a temperature control liquid circulating through the heat exchanger and the heater and/or cooler. The inventive method comprises using a long term disinfectant in the temperature control liquid, measuring and preferably recording the concentration of the disinfectant in the temperature control liquid and deducing a disinfectant status of the temperature control liquid from the measured concentration of the disinfectant in the temperature control liquid.

21 Claims, 1 Drawing Sheet

(51) Int. Cl.
*A61L 2/00* (2006.01)
*B01J 19/00* (2006.01)
*G01N 33/18* (2006.01)
*A61M 1/16* (2006.01)
*A61M 1/36* (2006.01)
*A61L 2/18* (2006.01)
*A61L 2/16* (2006.01)

(52) U.S. Cl.
CPC ............ *A61M 1/169* (2013.01); *A61M 1/367* (2013.01); *A61M 1/3666* (2013.01); *A61M 2205/366* (2013.01)

(58) Field of Classification Search
USPC .................. 422/1, 28, 38, 41, 43; 134/22.19; 210/749, 759, 764–766, 177; 604/4.01; 165/185
See application file for complete search history.

(56) References Cited

U.S. PATENT DOCUMENTS

| | | | |
|---|---|---|---|
| 5,409,612 | A | 4/1995 | Maltais et al. |
| 5,863,501 | A | 1/1999 | Cosentino |
| 5,871,526 | A | 2/1999 | Gibbs et al. |
| 6,981,794 | B2 | 1/2006 | Bibbo et al. |
| 7,900,629 | B2 | 3/2011 | Gurnee et al. |
| 8,231,664 | B2 | 7/2012 | Kulstad et al. |
| 8,343,202 | B2 | 1/2013 | Magers |
| 8,475,509 | B2 | 7/2013 | Dae |
| 2005/0047959 | A1 | 3/2005 | Brandl et al. |
| 2005/0284815 | A1* | 12/2005 | Sparks ................ A61M 1/1656 210/645 |
| 2011/0107251 | A1 | 5/2011 | Guaitoli et al. |
| 2013/0116761 | A1 | 5/2013 | Kreck |

FOREIGN PATENT DOCUMENTS

| | | | | |
|---|---|---|---|---|
| CN | 202154894 | U | 3/2012 | |
| CN | 102526822 | A | 7/2012 | |
| DE | 19531935 | A1 | 2/1997 | |
| DE | 19924856 | A1 | 12/2000 | |
| EP | 2698176 | A1 | 2/2014 | |
| EP | 2698177 | B1 | 2/2014 | |
| FR | 2631241 | * | 11/1989 | .............. A61M 5/44 |
| FR | 2631241 | A1 | 11/1989 | |
| JP | 54154195 | A | 12/1979 | |
| JP | 61131753 | A | 6/1986 | |
| JP | H1157733 | A | 3/1999 | |
| JP | 2003260131 | A | 9/2003 | |
| JP | 2005074236 | A | 3/2005 | |
| JP | 2005219041 | A | 8/2005 | |
| WO | 2009094601 | A2 | 7/2009 | |

OTHER PUBLICATIONS

International Preliminary Report of Patentability issed in PCT/EP2013/065602, completed Nov. 25, 2014, 15 pages.
International Preliminary Report on Patentability issued in PCT/EP2013/065601, completed Feb. 25, 2014, 7 pages.
International Search Report and Written Opinion issued in PCT/EP2013/065602, dated Sep. 24, 2013, 8 pages.
International Search Report and Written Opinionissued in PCT/EP2013/065601, dated Sep. 26, 2013, 9 pages.
International Preliminary Report on Patentabiiity issued in PCT/EP2014/067746, dated Mar. 2, 2017, 7 pages.
International Search Report and Written Opinion Issued in PCT/EP2014/067746, dated Dec. 1, 2014, 8 pages.

* cited by examiner

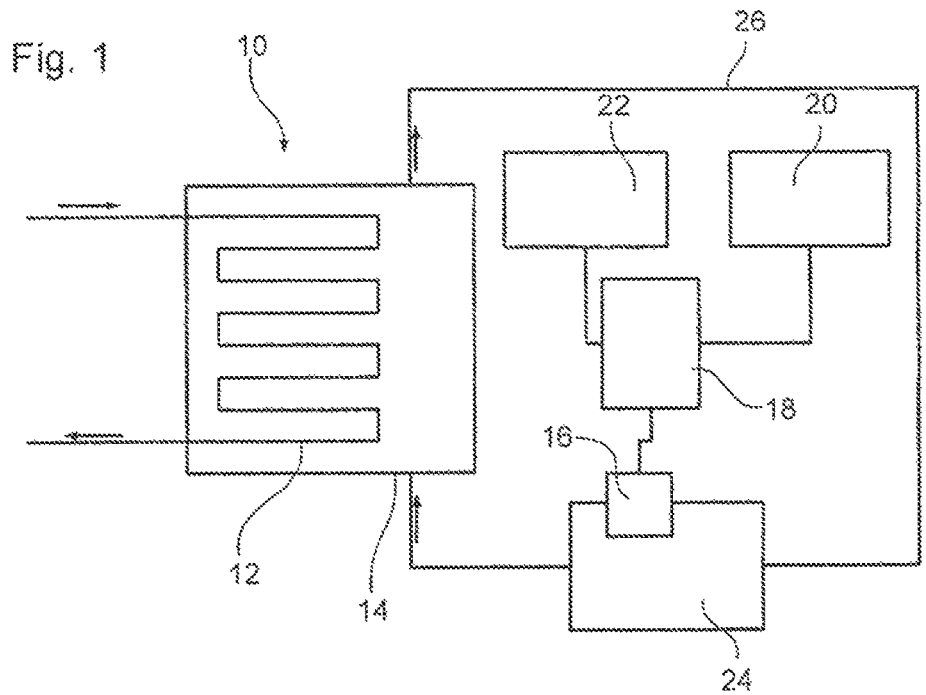
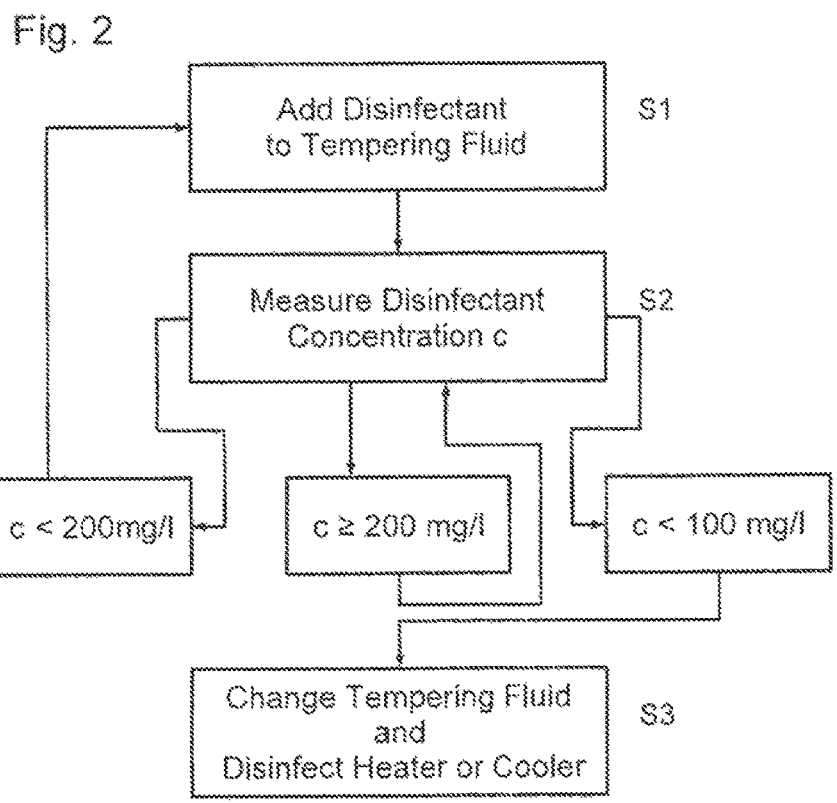

METHOD FOR CONTROLLING A DISINFECTION STATUS OF A TEMPERATURE CONTROL DEVICE AND TEMPERATURE CONTROL DEVICE FOR HUMAN BODY TEMPERATURE CONTROL DURING EXTRACORPOREAL CIRCULATION

CROSS-REFERENCE TO RELATED APPLICATIONS

This application is a continuation of U.S. application Ser. No. 14/421,438, internationally filed Jul. 24, 2013, which is a national phase application of PCT Application No. PCT/EP2013/065601, internationally filed Jul. 24, 2013, which claims priority to European Application No. 12 180 231.8, filed Aug. 13, 2012, all of which are herein incorporated by reference in their entirety.

TECHNICAL FIELD

The present invention relates to a method for controlling a disinfection status of a temperature control device, i.e. a heater and/or cooler for human body temperature control during extracorporeal circulation of blood. The temperature control is achieved by using a heat exchanger and temperature control liquid circulation through the temperature control device.

BACKGROUND

Extracorporeal circulation of blood is used in certain surgical procedures such as during heart surgery. During the extracorporeal circulation, the body temperature of the patient can be controlled, by controlling the temperature of the blood during extracorporeal circulation. For this purpose, a patient temperature control system can be provided by means of which the temperature of the blood of the patient in the circulation can be raised or lowered. The blood thus controlled, flows through the patient and the body of the patient approaches the temperature of the blood. So as to heat or cool the blood, the temperature control system comprises a heater and/or cooler device providing a liquid circulation to a disposable (single use) heat exchanger that transfers energy to and/or away from the patient's blood circulation. The liquid can be water.

The heat exchanger for the blood is a strict dual circuit system, the blood side and the liquid side being separated from each other so that any mixture, such as by means of diffusion, between the blood in one of the circuits and the temperature control liquid in the other of the circuits is inhibited as much as possible. Nevertheless, care has to be taken to avoid health risks stemming from the liquid.

SUMMARY OF INVENTION

The applicant has designed a mobile temperature control device for human body temperature control during extracorporeal circulation. Such a mobile device can be connected to a circuit of temperature control liquid to be used in a heat exchanger. The mobile temperature control device preferably is provided with exchangeable hoses or tubes or other conduits. Further, connecting and disconnecting these conduits can more easily be achieved if the conduits are not filled with the temperature control liquid during connecting and disconnecting. Likewise, it is preferred if the circuit can be emptied of temperature control liquid for the connection and disconnection of the mobile temperature control device. The preferred mobile device is consequently provided with an open reservoir where the temperature control liquid is exposed to environmental air. The temperature control liquid can be fed into the circuit from this reservoir and can be returned to it. Any air which might be trapped in one of the conduits during connecting or disconnecting the conduit and the temperature control device or the heat exchanger can be bled to the environment via the open reservoir. This means, however, that the temperature control liquid is exposed to the air of the environment.

Substances used as temperature control liquid, in particular water, are prone to microbial contamination when exposed to environmental air. If the temperature control liquid was exposed to the environmental air, disinfecting the temperature control device and the temperature control liquid can then improve the microbial status of the liquid and render the mobile device maintenance- and service-friendly.

In the prior art, disinfecting the temperature control device, i.e. the heater and/or cooler, was accomplished by regularly disassembling all devices and subjecting the disassembled parts to a separate disinfection procedure.

This was both time consuming and expensive. Further, it was required to establish a monitoring and recordation system in order to maintain and verify the disinfection status of the heater and/or cooler system within an acceptable range.

The invention addresses the need to more-easily maintain the microbial safety of the temperature control (heater and/or cooler) system.

This problem is solved by the inventive method according to claim 1 and the temperature control device according to claim 11. Further advantageous features and embodiments are defined in the dependent claims.

The heat exchanger for the inventive method pertaining to the above mentioned technical field comprises a blood side circulating blood and a liquid side circulating a temperature control liquid, for example water, wherein heat can be exchanged between the temperature control liquid on the liquid side and the blood on the blood side. Further, the blood side and the liquid side are separate from each other. The heat exchanger itself is a single-use device. After the operation of the patient, the heat exchanger is disposed. However, the temperature control device is a multi-use device and must be maintained in a disinfected state.

The method according to the invention comprises using a disinfectant in the temperature control liquid, measuring a concentration of the disinfectant in the temperature control liquid and deducing a disinfection status of the temperature control liquid from the measured concentration of the disinfectant in the temperature control liquid. Preferably, the concentration of the disinfectant in the temperature control liquid is not only measured but also recorded. Further preferably, the concentration of the disinfectant in the temperature control liquid is continuously measured.

According to the inventive method, the disinfectant is contained in the temperature control liquid during the use of the heater and/or cooler for human body temperature control. The measurement of the concentration of the disinfectant in the temperature control liquid allows for assessing the hygienic disinfection status of the temperature control liquid and, thus, the heater and/or cooler and also the heat exchanger. Since this information as to the hygienic status of the heater and/or cooler can be gained continuously, the disinfection status can also be continuously monitored and recorded and, hence, provides for a systematic assessment and monitoring of the hygienic development of the heat exchanger.

In connection with the present invention the term "human" means mammal or human and animal. It is to be noted that the inventive disinfection method is completely conducted outside of the human or animal body. A disinfectant in connection with the described invention is a disinfecting substance which can be, and preferably is, permanently present in the temperature control liquid without being hazardous to the patient during extracorporeal circulation and without damaging a (plastic) heat exchanger or other part of the circuit for extracorporeal circulation. As long as the concentration of the disinfecting substance in the temperature control liquid is above a certain minimum concentration, the substance is considered a disinfecting substance as the circuit is then in a disinfected state. The disinfectant could also be called a "long term disinfectant" and can optionally be defined by a maximum concentration in the temperature control liquid. "Long term" is an individual period of time without a precise minimum or maximum. Any disinfectant which, in its specific concentration in the temperature control liquid, can be used during the extracorporeal circulation and which does not require the circulation to be stopped for it being used for disinfection without being hazardous to the patient and without damaging the heat exchanger or any other part of the circuit for extracorporeal circulation is considered a long term disinfectant in the sense of the present application. One example for such a disinfectant is hydrogen peroxide preferably of a concentration of less than 500 mg/l and more than 100 mg/l.

Preferably, the disinfectant is at least one of hydrogen peroxide, sodium hypochlorite and citric acid, wherein hydrogen peroxide is particularly preferred. These disinfectants are under certain conditions not too critical in terms of a possible harm to material or health, if a leak in the heat exchanger should occur and some of the temperature control liquid should leak to the blood side and are, thus, particularly suitable to be used as long term disinfectants. This particularly relates to hydrogen peroxide. Laboratory tests have shown that the concentration of hydrogen peroxide reduces over time and, further, that the rate of absorption of the hydrogen peroxide may serve as an indicator for microbial contamination of the temperature control liquid. This means that monitoring the concentration of the disinfectant, particularly the hydrogen peroxide, in the temperature control liquid permits indirectly monitoring the microbial contamination of the temperature control liquid and, hence, the necessity of further disinfection of the temperature control device, namely the heater and/or cooler.

Preferably, the temperature control liquid includes water. More preferably, the temperature control liquid consists of water and the disinfectant as well as unavoidable contaminants. Using water as the temperature control liquid is preferable amongst others because of its wide availability. A further advantage of water is that it is considered harmless by the U.S. Food and Drug Administration (FDA). At the same time, water can easily be handled using only standardized equipment which reduces cost, if compared with liquids which require any specific equipment. The term "water" in connection with the present invention means drinking water. This implies a standardized quality and cleanliness of the water which is considered sufficient for using the water as temperature control liquid in a heat exchanger and a corresponding heater and/or cooler for human body temperature control during extracorporeal circulation. Further, water is compatible with many long term disinfectants and, hence, allows for choosing the disinfectant from a large group of potential long term disinfectants.

It is advantageous to measure the concentration of the disinfectant, in particular the hydrogen peroxide, during extracorporeal circulation while conducting the human body temperature control of the temperature control device, namely the heater and/or cooler, in order to deduce the disinfection status of the temperature control liquid and the heater and/or cooler at the same time as using the heater and/or cooler. This makes a separate assessment step for the heater and/or cooler in which the heater and/or cooler must not be used, unnecessary.

According to an advantageous method, the concentration of the disinfectant is maintained to range from 200 to 300 mg/l.

This concentration of the disinfectant, particularly hydrogen peroxide, provides for keeping the contamination of the temperature control liquid, for example water, in the temperature control device in an acceptable range. Such an acceptable range would be less than 100 CFU/ml. Further preferably, the amount of microbial contamination of the temperature control liquid is deduced from the concentration of the disinfectant in the temperature control liquid as a particularly significant aspect of the disinfection status of the temperature control liquid and, hence, the temperature control device, namely the heater and/or cooler.

Preferably, a rate of reduction of the concentration of disinfectant in the temperature control liquid is monitored and, further preferably, recorded. As the rate of absorption of the hydrogen peroxide can be used as an indicator for microbial contamination of the temperature control liquid, monitoring and recording the rate of reduction of the concentration of disinfectant in the temperature control liquid provides for reliable and statistically analyzable information on the contamination of the temperature control liquid.

According to a further advantageous method, it is judged that the temperature control liquid is sufficiently disinfected, if the concentration of disinfectant in the temperature control liquid is at least 200 mg/l. This concentration of a disinfectant, for example hydrogen peroxide, means that the contamination of the temperature control liquid is below the respective threshold and therefore acceptable.

According to a further preferred method, it is judged that the temperature control liquid is insufficiently disinfected, if the measured concentration of the disinfectant in the temperature control liquid is between 100 mg/l and 200 mg/l. The reduced concentration of disinfectant, such as hydrogen peroxide, in the temperature control liquid indicates an unacceptable level of contamination in the temperature control liquid and the temperature control device (the heater and/or cooler). The amount of contamination is, however, still within a range which is considered as a range of minor contamination.

The contamination of the temperature control device and the temperature control liquid can be reduced to an acceptable level by preferably further adding long term disinfectant such as hydrogen peroxide to the temperature control liquid so as to increase the disinfectant concentration in the temperature control liquid to at least 200 mg/l. The addition of the relatively harmless disinfectant, i.e. hydrogen peroxide, sodium hypochlorite or citric acid, allows for reducing the contamination of the temperature control liquid to an acceptable level while, at the same time, the temperature control device can be used for conducting the temperature control even considering a possible leaking of liquid out of the heater and/or cooler to a sterile room or even to the blood side of the heat exchanger.

It is further preferred that it is judged that the temperature control liquid is insufficiently disinfected, if the measured concentration of disinfectant in the temperature control liquid is 100 mg/l or less and it is further preferred at this concentration that the temperature control liquid is changed and that the temperature control device is disinfected with disinfectant of a concentration of at least 1000 mg/l. The disinfection of the temperature control device with the disinfectant of a concentration of at least 1000 mg/l is preferably not conducted during use of the heater and/or cooler in order to minimize any risk to the patient during the disinfection step since this concentration of disinfectant might no longer be considered harmless so that the disinfectant might no longer be considered as a long term disinfectant.

If the last measurement of the disinfectant concentration in the temperature control liquid is 14 days or more ago, the temperature control liquid is preferably changed and the temperature control device, i.e. the heater and/or cooler, is disinfected using a sodium hypochlorite solution.

In order to determine the concentration of disinfectant in the temperature control liquid, a disinfectant sensor is preferably used providing an electric signal in accordance with the concentration of the disinfectant in the temperature control liquid. In particular, the disinfectant sensor is a hydrogen peroxide sensor generating an evaluation of the hygienic status of the temperature control device.

A temperature control device for human body temperature control extracorporeal circulation according to the present invention comprises a disinfectant sensor configured for measuring a concentration of disinfectant in the temperature control liquid. The temperature control device is a heater and/or cooler.

Such a heater and/or cooler provides for the continuous determination of its disinfection status during use in human body temperature control and allows for solving the problems mentioned before.

Preferably, the temperature control device is connected to a first display which is configured for indicating whether the concentration of the disinfectant in the temperature control liquid is (a) at least 200 mg/l, (b) between 100 mg/l and 200 mg/l or (c) 100 mg/l or below. The display is configured for indicating the concentration of the disinfecting which allows for deducing the disinfection status of the temperature control liquid and the hygienic status of the heater and/or cooler.

Alternatively or additionally, the temperature control device is preferably connected to a second display which is configured for indicating whether the disinfection status of the temperature control liquid is satisfactory, whether disinfectant is to be added or whether the temperature control liquid is to be exchanged. Naturally, also a single display can be provided which is configured for indicating the concentration of the disinfectant as well as the hygienic status and the modifications to be applied to the system, at the same time.

The method and the device according to the present invention simplify maintenance of the hygienic status of the device and facilitate a recording/monitoring system to be established which allows for proving the hygienic status continuously over time and determining trends or developments in the hygienic status of the heater and/or cooler. The absorption rate of the hydrogen peroxide or other disinfectant can be recorded and used for determination of the contamination status. In this respect, a high absorption rate of hydrogen peroxide indicates microbial contamination. This is an advantage over discrete measurements conducted in relatively long intervals because such discrete measurements cannot sufficiently exactly produce information as to the gradient of absorption of the disinfectant.

As sensors for the disinfectant, in particular hydrogen peroxide, particularly preferred sensors include conductance sensors or electrochemical sensors such as a Clark cell. In particular, the heater and/or cooler can be prepared for use of several different sensors for measuring the concentration of hydrogen peroxide or other disinfectant.

In conclusion, the invention allows for an indirect measurement of the contamination of the heater and/or cooler and the temperature control liquid in the heater and/or cooler as well as the heat exchanger on its temperature control liquid side. This makes the time-consuming and expensive direct measurements of the contamination unnecessary which to date use germ spreads. Accordingly, the invention allows for a significant facilitation of maintenance, monitoring and control of the hygienic status of a heater and/or cooler for an extracorporeal circulation of blood during a surgical operation.

Reference is made to the co-assigned patent application EP 12 180 230.0 filed Aug. 13, 2012, entitled "Method and apparatus for disinfection of a temperature control device for human body temperature control during extracorporeal circulation", the complete content of which is hereby incorporated herein.

This co-assigned patent application describes and claims a method for disinfection of a temperature control device for human body temperature control during extracorporeal circulation which uses a long term disinfectant. The method and apparatus described in the co-assigned patent application can preferably be combined with the invention described in the present application, in particular in that the addition of disinfectant to the temperature control liquid can be based on the method and device disclosed in the present application. In other words, the method and device disclosed in the co-assigned patent application can be combined with the invention disclosed in the present application. This particularly facilitates performing a fully-automatic or at least semi-automatic disinfection method based on the information obtained by the method and/or device of the present application.

In particular, the outcome of the method for controlling the disinfection status of a temperature control device of the present application can be that the disinfection status of the temperature control device is insufficient. In this case, the method of disinfection as described in the co-assigned application can be used for improving the disinfection status of the temperature control device.

BRIEF DESCRIPTION OF THE DRAWINGS

FIG. 1 shows a schematic diagram illustrating a temperature control device in a heat exchanging system according to a preferred embodiment.

FIG. 2 shows a diagram illustrating a preferred method for controlling the disinfection status of a temperature control device.

DETAILED DESCRIPTION

FIG. 1 shows a schematic diagram of a heat exchanger 10 for human body temperature control during extracorporeal circulation. The heat exchanger 10 comprises a blood side 12 and a temperature control liquid side 14 in which blood and a temperature control liquid are respectively circulated.

The temperature of the temperature control liquid used in the heat exchanger 10 is controlled by a heater and/or cooler 24, i.e. a temperature control device. The heater and/or cooler 24 is a device which is capable of heating or cooling or heating and cooling the temperature control liquid. Preferably, the heater or cooler is capable of both heating and cooling the temperature control liquid so that a defined temperature of the temperature control liquid can be maintained. The heater and/or cooler 24 is part of a temperature control liquid side circuit 26 in which the temperature control liquid is circulated for operating the heat exchanger 10 in controlling the temperature of the human body of a patient.

The heater and/or cooler 24 is provided with a disinfectant sensor 16 configured for measuring a concentration of a disinfectant in the temperature control liquid in the heater and/or cooler 24. The result of the measurement of the sensor 16 is transmitted to a computer 18 which controls a first display 20 indicating the measured concentration of disinfectant in the temperature control liquid and a second display 22 indicating the consequence of the measured concentration. In particular, the second display 22 indicates whether the disinfection status of the temperature control liquid is satisfactory, whether further disinfectant is to be added or whether the temperature control liquid is to be exchanged.

FIG. 2 shows a diagram illustrating a preferred method. In a first step S1, disinfectant is added to the temperature control liquid in the heater and/or cooler. An example for the disinfectant is hydrogen peroxide. As a second step S2, the concentration C of the disinfectant is measured, for example by a specific sensor for the respective disinfectant.

The measuring of the disinfectant concentration C may result in C being at least 200 mg/l. This result means that the concentration C is within an acceptable range and the disinfectant concentration C is further continuously measured.

Another result from the measurement of the disinfectant concentration can be that C is between 100 and 200 mg/l. In this case, the disinfectant concentration C is below the acceptable level but still within a range of minor contamination so that further disinfectant is provided to the temperature control liquid in step S1. The disinfectant concentration C is further continuously measured and the disinfectant is added to the temperature control liquid until the disinfectant concentration is at least 200 mg/l, preferable between 200 and 300 mg/l.

A third measurement result of step S2 can be that the concentration C is below 100 mg/l. In this situation, the temperature control liquid is changed in step S3 and the heater and/or cooler is thoroughly disinfected using disinfectant of a concentration of at least 1000 mg/l or using another disinfectant such as a sodium hypochlorite solution.

The invention claimed is:

1. A method for controlling a disinfection status of a temperature control device for human body temperature control during extracorporeal circulation, wherein temperature control is achieved by use of the temperature control device that circulates the temperature control liquid through a heat exchanger, the method comprising:
measuring a concentration of a disinfectant in the temperature control liquid continuously during the extracorporeal circulation;
generating by a computer a disinfection status of the disinfectant from the measured concentration to be one of sufficiently disinfected, minor contamination, and change temperature control liquid; and
generating by the computer an adjustment recommendation in response to the disinfection status during the extracorporeal circulation.

2. The method of claim 1, wherein measuring a concentration comprises measuring the concentration of the disinfectant in the temperature control liquid via a disinfectant sensor.

3. The method of claim 2, wherein the disinfectant sensor is situated in the temperature control device.

4. The method of claim 2, wherein the disinfectant sensor provides an electric signal in accordance with the concentration of the disinfectant.

5. The method of claim 1, wherein generating the disinfection status comprises:
assigning the disinfection status to sufficiently disinfected if the concentration of the disinfectant is at least a first concentration;
assigning the disinfection status to minor contamination if the concentration of the disinfectant is between the first concentration and a second concentration; and
assigning the disinfection status to change temperature control liquid if the concentration of the disinfectant is less than or equal to the second concentration.

6. The method of claim 1, further comprising:
recording the concentration of the disinfectant and determining a rate of reduction of the concentration of the disinfectant in the temperature control liquid.

7. The method of claim 1, wherein the disinfectant comprises at least one of hydrogen peroxide, sodium hypochlorite and citric acid.

8. The method of claim 1, wherein the temperature control liquid includes water.

9. The method of claim 1, wherein generating the adjustment recommendation if the disinfection status is minor contamination comprises indicating adding disinfectant to the temperature control liquid to increase the concentration of the disinfectant in the temperature control liquid to at least the first concentration.

10. The method of claim 1, wherein generating the adjustment recommendation if the disinfection status is change temperature control liquid comprises indicating changing the temperature control liquid and disinfecting the temperature control device with disinfectant having a third concentration that is greater than the first concentration.

11. The method of claim 1, wherein the temperature control liquid is provided from and returned to a reservoir.

12. The method of claim 1, further comprising:
indicating the concentration of the disinfectant on a first display connected to the temperature control device.

13. The method of claim 1, further comprising:
indicating the disinfectant status on a second display connected to the temperature control device.

14. A method for controlling a disinfection status of a temperature control device for human body temperature control during extracorporeal circulation, wherein temperature control is achieved by use of the temperature control device that circulates a temperature control liquid through a heat exchanger, the method comprising:
measuring and recording a concentration of a disinfectant in the temperature control liquid continuously during the extracorporeal circulation;
calculating by a computer a rate of reduction of the concentration of the disinfectant in the temperature control liquid during the extracorporeal circulation; and
determining a level of contamination based on the rate of reduction of the concentration.

15. The method of claim 14, comprising:
   determining a disinfection status of the temperature control liquid from the concentration of the disinfectant in the temperature control liquid.

16. The method of claim 14, wherein measuring the concentration includes use of a disinfectant sensor.

17. The method of claim 14, further comprising:
   generating a disinfection status of the disinfectant from the measured concentration to be one of sufficiently disinfected, minor contamination, and change temperature control liquid.

18. The method of claim 17, further comprising:
   generating an adjustment recommendation in response to the disinfection status during the extracorporeal circulation.

19. A system including a temperature control device for human body temperature control during extracorporeal circulation, which can be connected to a heat exchanger and is configured for heating and/or cooling a temperature control liquid to be circulated through the heat exchanger for achieving the human body temperature control, the system comprising:

a disinfectant sensor configured to measure a concentration of a disinfectant in the temperature control liquid during the extracorporeal circulation;

a computer configured to receive the measured concentration, generate a disinfection status of the temperature control liquid, the disinfection status being from a group including a first status, a second status, and a third status, and generate an adjustment recommendation in response to the disinfection status during the extracorporeal circulation; and at least one display controlled by the computer to indicate the disinfection status and the adjustment recommendation.

20. The system of claim 19, wherein the disinfectant sensor is situated in the temperature control device.

21. The system of claim 19, wherein the heat exchanger comprises a blood side circulating blood and a liquid side circulating the temperature control liquid separate from each other and configured to exchange only heat.

* * * * *